United States Patent [19]
Walker et al.

[11] Patent Number: 4,934,386
[45] Date of Patent: Jun. 19, 1990

[54] APPARATUS FOR ASSESSING RESPONSES OF HUMANS TO STIMULANTS

[75] Inventors: James C. Walker; Daniel B. Kurtz; Ford M. Shore, all of Winston-Salem, N.C.

[73] Assignee: R. J. Reynolds Tobacco Company, Winston-Salem, N.C.

[21] Appl. No.: 107,609

[22] Filed: Oct. 13, 1987

[51] Int. Cl.$^5$ ...................... A24F 47/00; G09B 19/00
[52] U.S. Cl. ..................................... 131/329; 434/236
[58] Field of Search ................ 131/290, 329; 434/309, 434/236

[56] References Cited
U.S. PATENT DOCUMENTS
4,468,204  8/1984  Scott et al.
4,543,957  10/1985 Friedman et al.
4,582,492  4/1986  Etter et al.

OTHER PUBLICATIONS

Stordeur et al., *J. Air Poll. Cont. Assoc.*, vol. 31, pp. 377–380 (1981).
Benignus et al., *Behav. Res. Meth. & Instr.*, vol. 12, pp. 535–540 (1980).
Laing, *Perception*, vol. 12, pp. 99–117 (1983).
Laing, *Physio. & Behavior*, vol. 34, pp. 569–574 (1985).
Cain et al., *Atmospheric Environment*, vol. 21, pp. 347–353 (1987).

*Primary Examiner*—V. Millin

[57] ABSTRACT

Two olfactometers can simultaneously but independently provide stimulation to the eyes and nose of a human subject. Thus, a sample of air containing an odorant is delivered to the eyes only, nose only, or both eyes and nose of the subject. Physiological responses such as eye blink rate and breathing rate are observed and automatically recorded. Psychophysical responses such as ratings of ocular or nasal irritation also are recorded. The apparatus is useful in collecting data regarding fragrances and environmental air quality.

37 Claims, 5 Drawing Sheets

APPARATUS FOR ASSESSING RESPONSES OF HUMANS TO STIMULANTS

BACKGROUND OF THE INVENTION

The present invention relates to the assessment of psychophysical and physiological responses of a human subject to stimuli delivered to that subject's nose and/or eyes.

Recent interest in air quality has made it desirable to quantify the responses of humans to a wide range of the constituents which can be present in the atmosphere. Some of the constituents of the environmental air may be regarded as pollutants. However, the levels of certain pollutants, irritants or odorants in the atmosphere are oftentimes very low. Thus, it is difficult to reliably present to a human subject such constituents at the concentrations actually present in the environment. Also, it is difficult to fully characterize the responses of human subjects to these constituents using both psychophysical and physiological measurements.

Additionally, recent interest in the development of flavors and fragrances has required efficient and effective means for characterizing particular flavors and fragrances at low levels in environmental air. Such characterization of certain flavors and fragrances is often performed using human subjects. Stordeur et al, *J. Air Poll. Cont. Assoc.*, Vol. 31, p. 377 (1981) propose a microprocessor-controlled dynamic olfactometer. The proposed device reportedly supplies air containing controlled amounts of odorant samples to the nose of a human subject. The human subject then can comment regarding the odorous stimuli which were provided by the air sample. However, the reference does not propose a device which can provide for the measurement of physiological responses (e.g., changes in breathing rate). In addition, the proposed device does not provide stimulus to the eyes of the subject.

Benignus et al, *Behav. Res. Meth. & Instr.*, Vol. 12, p. 535 (1980) propose a computer-controlled vapor dilution olfactometer. However, the reference proposes only providing an air sample to the nose of the human subject.

Laing, *Perception*, Vol. 12, p. 99 (1983) and *Physio. & Behav.*, Vol. 34, p. 569 (1985) proposes an apparatus for testing the sniffing behavior of human subjects. However, the subject is allowed to sample a gaseous material through his/her mouth.

Cain et al, *Atmos. Envir.*, Vol. 21, p. 347 (1987) proposes applying a sample of environmental tobacco smoke to the face of a subject. The reference does not propose recording physiological responses of the subject.

It would be highly desirable to provide an apparatus for providing controlled samples of air, which contains known concentrations of odorant independently to the eyes and nose of a subject. In addition, it would be desirable to obtain both physiological and psychophysical responses of the subject to the stimulus provided by the air sample.

SUMMARY OF THE INVENTION

The present invention relates to an apparatus which is capable of providing simultaneous but independent stimulation of the eyes and/or nose of a human subject. The stimulation is controlled in that a controlled amount of stimulant is contained in a flow of air of controlled volume flow rate. The apparatus includes a source of stimulant and means for transferring controlled amounts of the stimulant to the eyes and/or nose of the human subject. The apparatus also includes a means for altering the identity and amount (e.g., concentration) of the stimulant which is transferred to the eyes and/or nose of the subject. Preferably, the delivery of a controlled amount of the particular stimulant is transferred independently to the eyes and/or nose of the subject, and is automatically controlled using computer means. The apparatus also includes (i) means for recording psychophysical responses of the subject to the stimulant, and (ii) means for recording physiological responses of the subject to the stimulant.

The apparatus of this invention is useful for allowing the skilled artisan to collect data concerning the ability of humans to detect, recognize, discriminate or assign qualitative labels to either single compounds or mixtures of compounds which may be stimulants when present in environmental air. Such an apparatus allows the eyes and nose of a human subject to be exposed simultaneously and independently to air samples containing accurately monitored and controlled amounts of stimulant. The apparatus then provides for the recordation of that subject's response to each individual air sample. For example, the subject can comment on the stimulation provided (i.e., provide a psychophysical response).

The preferred embodiment of this invention includes a computer means for collecting such responses, as well as for controlling the production and transfer of the stimulus. Thus, the computer means can track the subject's responses and utilize those responses to determine and control the subsequent stimulation which is provided to the subject. As a result, the automated apparatus of this invention can be continuously employed in a manner which is not highly labor intensive.

Furthermore, changes in breathing rate, eye blinking, eye tearing and the like (i.e., physiological responses) can be monitored as the subject is exposed to the stimulant. Such responses can be recorded using video camera, by means for measuring changes in breathing rate, or the like.

For the most preferred embodiment, separate nasal and ocular olfactometers each independently provide controlled volume flow rates of gaseous samples to the nose and eyes, respectively. Thus, the apparatus of this invention is useful in that stimulation using airborne stimuli can be provided to the nose alone, the eyes alone, or both the eyes and the nose.

As used herein, the term "odorant" is meant to include any chemical compound or mixture of compounds that, when delivered in a gaseous or aerosol medium, can stimulate olfactory and/or trigeminal chemoreceptors in the nasal cavity and cause physiological and/or psychophysical responses.

As used herein, the term "stimulant" is meant any chemical compound or mixtures of chemical compounds that, when delivered in a gaseous or aerosol medium, can stimulate olfactory and/or trigeminal chemoreceptors in the nasal cavity and/or trigeminal chemoreceptors in the cornea and cause physiological and/or psychophysical responses.

DETAILED DESCRIPTION OF THE PREFERRED EMBODIMENTS

Figure 1:
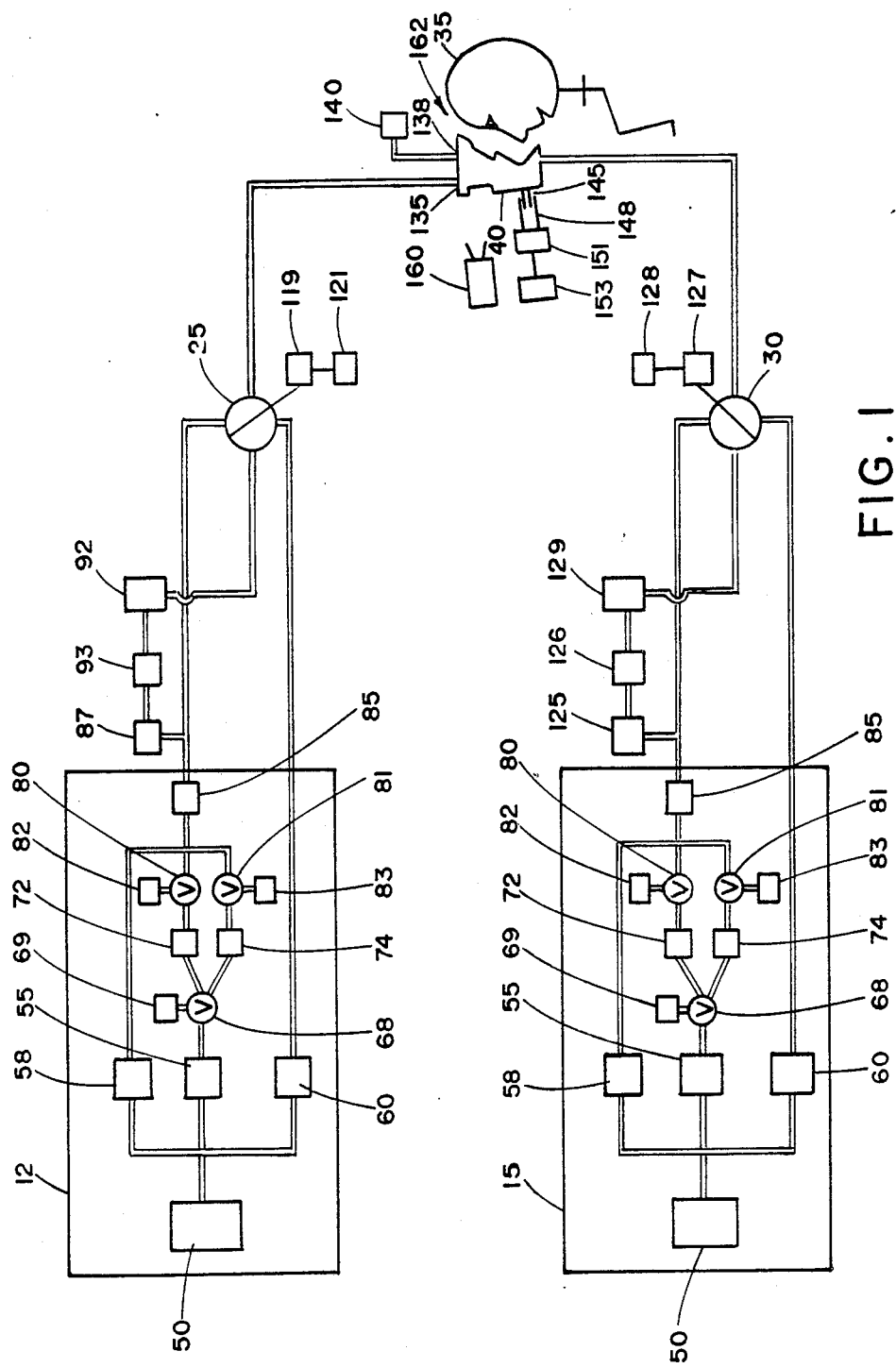
FIG. 1 is a schematic diagram of an ocular olfactometer, a nasal olfactometer, and the subject sampling area.

Referring to FIG. 1, the apparatus 10 includes an ocular olfactometer 12, a nasal olfactometer 15 and valves 25 and 30 or other suitable means for transferring the respective gaseous samples from the respective olfactometers 12 and 15, to the eyes and nose of human subject 35. The respective gaseous samples are independently delivered to the eyes and nose of the human subject 35 through a fitted mask 40, or other suitable means for accurately delivering the gaseous samples to the eyes and nose of the subject.

Ocular olfactometer 12 includes a source of air 50. A suitable air source 50 can be provided from a laboratory air line equipped with a molecular sieve air cleaner such that clean, dry air is provided at about 60 lb./sq. inch. A suitable air cleaner/dryer is commercially available as Model 737-12-A from Aadco, Inc., Clearwater, Fla. The air so provided is transferred using a suitable transfer and connection means such as polytetrafluoroethylene (Teflon) tubings and fittings. Adequate transfer means throughout the apparatus can be flexible Teflon tubing having about ¼ inch outer diameter and about 3/16 inch inner diameter.

The air so provided is passed through electronic mass flow controllers 55, 58 and 60 or other suitable means for providing a predetermined volume flow rate of air. Suitable mass flow controllers 55, 58 and 60 include those commercially available as Electronic Mass Flow Controller Series CST from Teledyne-Hastings, Inc. Hampton, Va. Flow controller 55 has a valve 68 positioned downstream therefrom in order to provide for airflow into odorant saturator tubes 72 and 74 as well as positive shut off of airflow when contact of the flowing air with the odorant is not desired. A suitable valve 68 is a Teflon-lined AC miniature solenoid valve commercially available as Model 1-35-900 from General Valve Corp., Fairfield, N.J. The positioning of valve 68 is controlled by switching mechanism 69, or other means for positioning the valve into an "open" or "closed" position. Preferably, the valve 68 is of the "latching" variety such that it may be changed from an open to a closed position, or vice versa, as a result of an AC pulse delivered to one input wire of the value by switching mechanism 69. Such a valve remains in its set position until a subsequent AC pulse from a separate input wire is received. An example of a suitable switching mechanism 69 for latching valve 68 is a pair of solid state AC switching relays sold commercially as Model 6411 by Crydom Controls Division of International Rectifier, El Segundo, Calif. The pair of switching relays for each valve provide for "open" and "closed" positioning of the valve, respectively. Assembly of the valve and switching mechanism will be apparent to the skilled artisan. Such a switching mechanism can be controlled using a computer means as described hereinafter.

Figure 2:
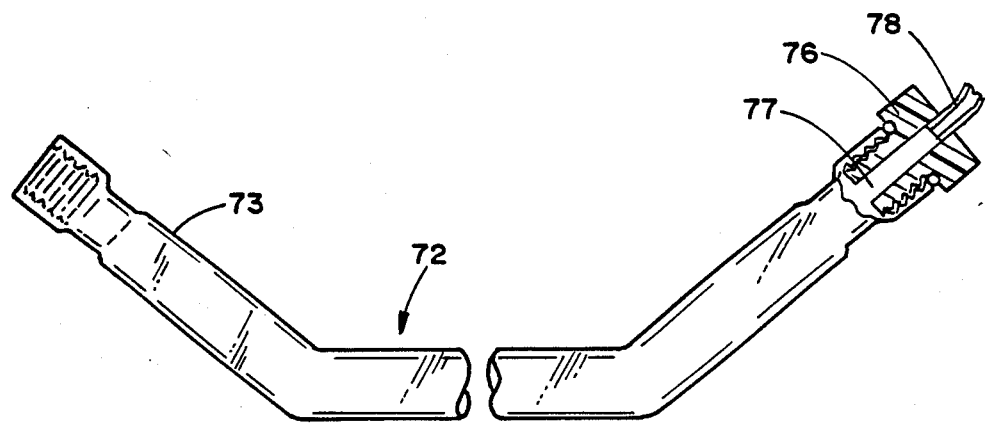
FIG. 2 is a longitudinal view of an odor saturator tube (a portion of which is cut away) and a sectional view of a connector positioned at one end thereof.

Referring to FIG. 2, a suitable odorant saturator means 72 is a glass tube 73 having a shape as shown. Such an odorant saturator means provides a suitable source of stimulant. A suitable tube 73 has an inner diameter of about 15 mm, and a total length of about 45 mm wherein each of the upwardly extending portions has a length of about 13 mm. Generally, tube 73 of such a size can contain about 2 ml to about 5 ml of liquid odorant which is positioned therein such that the liquid rests in the bottom region of the tube. The ends of tube 73 are equipped with connectors. As shown in FIG. 2, connector 76 is threaded into one end of tube 73. Connector 76 has a passageway 77 extending therethrough. Passageway 77 in turn provides for connection to tubing 78. Exemplory tubing 78 can be ⅛ inch outer diameter Teflon tubing. In such a manner, air flows into the tube 73, passes into contact with the odorant within the tube 73, and the air containing odorant exits the opposite end of the tube 73.

The temperature of the odorant saturator preferably is controlled by positioning the odorant saturator within a steady state controlled temperature unit (not shown). For example, an odorant saturator having the tubular configuration shown in FIG. 2 can be positioned in a water/propylene glycol temperature bath (not shown) such that the connective ends of the tube extend above the surface of the bath. The controlled temperature bath can be equipped with means for heating and cooling the odorant within the odorant saturator, centrifugal pumps, thermocouples, and the like. The assembly and operation of controlled temperature units will be apparent to the skilled artisan.

If desired, the olfactometer can have several odorant saturators (preferably assembled in a "parallel" manner) and can be equipped correspondingly with several mass flow controllers and shut off valves. Increasing the number of odorant saturators can provide an increase in the number of odorants which can be tested within a test session.

Referring again to FIG. 1, flow of odorant saturated air from the odorant saturators 72 and 74 is controlled by valves 80 and 81, respectively. Valves 80 and 81 preferably are of similar construction to the previously described valve 68. Valves 80 and 81 preferably are controlled by switching mechanisms 82 and 83, respectively. Switching mechanisms 80 and 81 preferably are of similar construction to the previously described switching mechanism 69.

Air which contains odorant passes through valves 80 and 81 into mixing chamber 85 which allows clean dry air from flow controller 58 to be mixed with odorant saturated air from flow controllers 72 and/or 74. An example of a mixing chamber is a tubular shaped member having a length of about 2 inches and an inner diameter of about 1 inch. In such a manner, the olfactometer 12 generates controlled volume flow rates of gas (e.g., air) and a predetermined, controlled concentration of a stimulant within that gas. The positioning of the various valves and the flow settings of the various mass flow controllers provide for the altering of the level of stimulant within the gaseous medium.

Monitoring of the olfactometer 12 output is provided by a photo-ionization detector 87, or other suitable means for physically monitoring the instantaneous concentration of the odorant present in the air sample produced by the olfactometer. A preferred photo-ionization detector is commercially available as PID Model PI-52 from HNU Systems, Newton, Mass. In operation, a small amount (e.g., about 10 percent or less) of the air sample is continuously monitored by the photo-ionization detector, and the sampled air is exhausted by a laboratory vacuum source 92 or other suitable exhaust means. An electronic mass flow controller 93 is positioned downstream from the photo-ionization detector in order to provide for determination and control of the volume flow rate of gaseous sample through the photo-ionization detector. The gaseous sample preferably is continuously monitored by the photo-ionization detector. Such continuous monitoring of the gaseous sample is desirable in order to (i) allow analytical verification of the olfactometer output; and (ii) provide a measure of safety in that the olfactometer can be shut off if odorant outputs exceed predescribed concentration limits.

Figure 3:
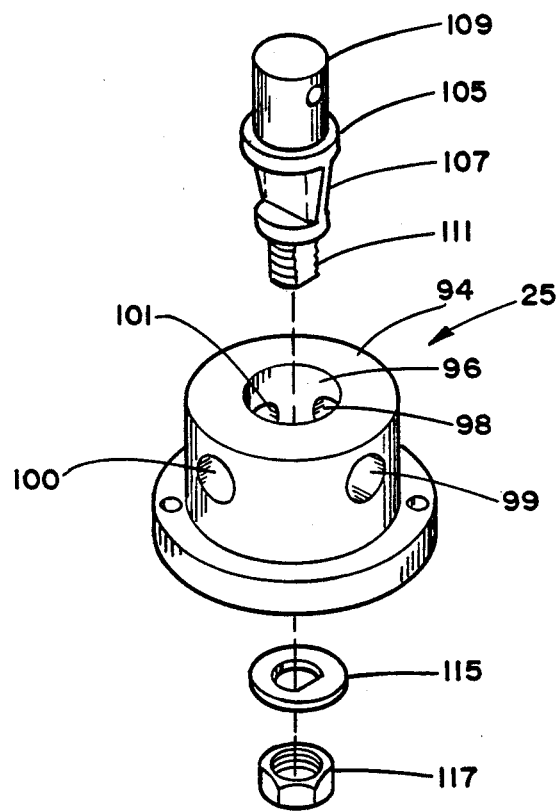
FIG. 3 is an exploded perspective of a flow valve useful in the apparatus of this invention.

Referring to FIG. 3, flow valve 25 is manufactured from Teflon or other suitable material. Preferred materials are those which neither retain the stimulants nor react with the stimulants. Valve 25 includes a body 94 having a central hollow region 96 into which four ports 98, 99, 100 and 101 extend. Typically, the four ports are positioned at 90° intervals relative to one another. Preferably, the central hollow region is slightly tapered such that blade portion 105 can fit snugly therein. Blade portion 105 includes a thin blade 107 which can be rotated within the central hollow region 96, an upper region 109 which extends above the body 96 such that the blade can be rotated, and a bottom region 111 which can be threaded. The bottom region 111 allows the blade portion 105 to be maintained within the body 94 of the valve. In particular, the threaded bottom region 111 can be fitted with washer 115 and bolt 117, or other suitable fastening means. Flow valve 25 having a configuration as shown in FIG. 3 is desirable in order that no interruption in airflow to the subject occurs during operation. Manufacture and operation of such flow valves will be apparent to the skilled artisan. See, Walker et al, Physiol. & Behav., Vol. 38 p. 575 (1986); and Oley et al, *J. Comp. & Physiol. Psychol.*, Vol. 88, p. 477 (1975).

Referring again to FIG. 1, valve 25 can be controlled such that clean air from flow controller 60 is passed to the subject 35 or air having a controlled amount of odorant is passed to the subject. As shown in FIG. 1, the valve 25 is positioned such that an air sample having odorant therein is passed to the eyes of the subject, and clean air is directed to exhaust means 92 (i.e., the valve is positioned to allow passage of airflow from the odorant output channel of the olfactometer to the subject).

Valve 25 is operated using a pneumatic cylinder 119, or other suitable means for rotating the blade 107 within the hollow region 96 of the body 94 of the valve (see FIG. 3). For example, pneumatic cylinder 119 connected to the blade of the valve 25 can rotate the blade back and forth at 90° intervals in order that the passage of selected airflows can be accomplished. A suitable pneumatic cylinder is available as Model 04DPRX3.00 from Compair Tools and Controls, Inc., Kittery, Me. The positioning of the pneumatic cylinders, and hence the positioning of the valve 25, is accomplished by switching mechanism 121. An example of a suitable switching mechanism 121 is a pair of solid state AC switching relays (as described hereinbefore). The pair of switching relays for the pneumatic cylinder provide for the "extended" or "retracted" positioning of the piston of the pneumatic cylinder. The extension or retraction of the piston in turn provides for the desired positioning of the blade within the valve housing.

Nasal olfactometer 15 has a construction similar to that of previously described ocular olfactometer 12, and like components are identified in FIG. 1 by like reference numerals. In addition, the output of the nasal olfactometer is monitored by a photo-ionization detector 125. An electronic mass flow controller 126 is positioned downstream from the photo-ionization detector 125. Valve 30 preferably has a similar construction to previously described valve 25. Valve 30 is controlled by pneumatic cylinder 127 and switching mechanism 128, which are similar to previously described pneumatic cylinder 119 and switching mechanism 121, respectively. As shown in FIG. 1, the valve 30 is positioned such that clean air is directed to the nose of the subject 35, and an air sample which may have odorant therein is directed to exhaust means 129 which is similar to previously described exhaust means 92 (i.e., the valve is positioned to allow passage of airflow from the clean air output channel of the olfactometer to the subject).

The airflows from each of the ocular and nasal olfactometers are delivered to the eyes and nose of the subject 35 through mask 40. The mask preferably is custom fitted for the user in order that minimal air loss is experienced in the facial area of the subject 35 during testing. As such, stimulation of the eyes and stimulation of the nose can be provided in a controlled manner. Airflow from ocular olfactometer 12 enters the ocular region of the mask through at least one input passage 135. Airflow then is exhausted through at least one output passage 138 to exhaust means 140. Airflow from nasal olfactometer 15 enters the nasal region of the mask through input passage 143 and is exhausted through output passage 145. The output passage 145 is equipped with tubular member 148 such that pneumotachograph 151, or other suitable means for monitoring breathing of the subject 35, can be positioned downstream from the subject. A suitable pneumotachograph 151 is a Fleisch pneumotachograph which is commercially available as Model 7319, type 1, size No. 1 from OEM Medical, Richmond, Va. The pneumotachograph is positioned downstream from the subject and provides a means for monitoring the change in the flow of the air which occurs as the subject breathes. The air exiting the pneumotachograph 151 is exhausted by exhaust means 153.

A video camera 160 is positioned so as to be focused at the eyes of the subject. In such a manner, physiological responses of the eyes of the subject (e.g., blinking, tearing, etc.) can be recorded during the stimulation presentation period. A suitable video camera 160 is an RCA Model TC2011U having 12.5 mm lens. The signal from the video camera can be split in order that the subject can be viewed by a session coordinator on a television screen (not shown) and the physiological response of the subject's eyes can be recorded on a video cassette recorder (not shown).

The subject is tested in test session area 162. Preferably, the test session area is separated from the remainder of the apparatus in order to avoid diversion of the subject's concentration during testing. For example, the mask 40 can be mounted within a partition (not shown) which forms a test booth or other means for surrounding the subject. The computer monitor and means for obtaining psychophysical responses of the subject can be positioned within the booth and adjacent to the partition.

Figure 4:
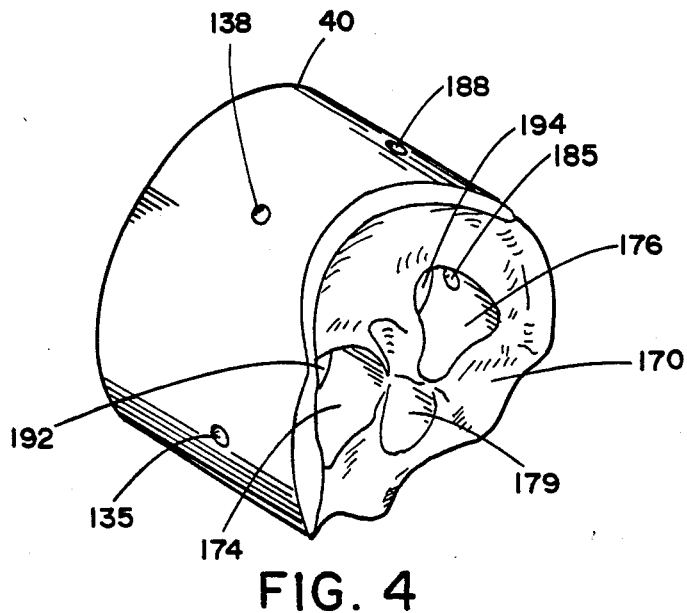
FIGS. 4 and 5 are perspectives of the mask into which the subject's face is positioned.
Figure 5:
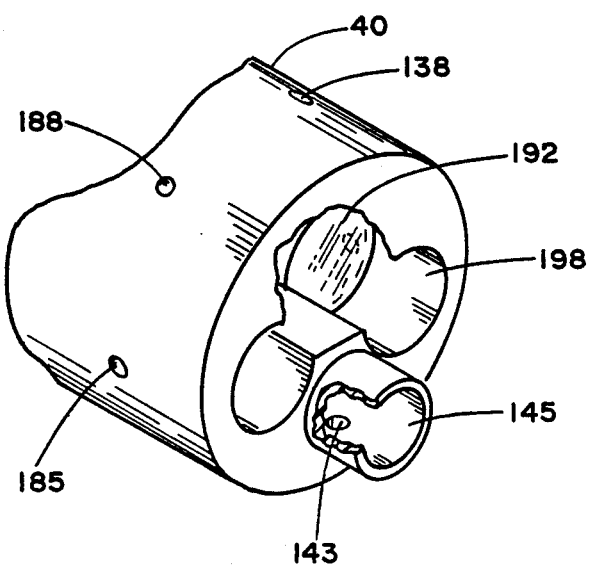

Referring to FIGS. 4 and 5, mask 40 preferably has a surface 170 which is custom fitted to the face of the subject. Regions 174 and 176 are openings to expose the subject's eyes; and region 179 is fitted to the subject's nose. Mask 40 includes input passages 135 and 185 which allow gaseous samples to be directed to the eyes of the subject; and output passages 138 and 188 which allow the gaseous samples to be exhausted. The region surrounding the eyes of the subject is contained by clear glass disks 192 and 194 which snugly fit within the mask adjacent to regions 174 and 176, respectively. The face of the mask opposite custom fitted surface 170 has an open region 198 (shown as partially cut away in FIG. 5) to expose the eyes of the subject. In such a manner, physiological data regarding the subject's eyes can be obtained during a test session. The mask also includes input passage 143 from nasal olfactometer and output passage 145 (shown as partially cut away in FIG. 5).

A suitable mask can be manufactured by machining a cylinder (e.g., having a diameter of about 6 inches) from a material which does not retain or react with the odorants which are ultimately delivered. Examples of suitable materials are Delrin and Teflon which are available from E.I. duPont de Nemours, Inc., Wilmington, Del. Such a mask can be manufactured using techniques available to the skilled artisan. For example, an impression of the subject's face can be made using dental alginate. The facial impression can be digitized and stored on computer. The digitized coordinates of the impression can be input into a computer-controlled milling apparatus which machines the facial impression of the subject from a Delrin or Teflon cylinder. Typically, the passageways for the eyes and nose of the subject then are machined into the mask. A Mitutoyo Coordinate Measuring Machine (model B231, MTI Corp.; Irving, Tex.) which utilizes a Renishaw touch probe (model PH8, Renishaw; Glos., England) suitably is used for the recording of the X-Y-Z coordinates from the impression. The digitizing process conveniently is completed by means of a program within the Ulticam 2000 package (N.C. Graphics; Cambridge, England/Hurco Manufacturing Co.; Indianapolis, Ind.). The Ulticam 2000 CAD/CAM software can be run on a Kontron graphics terminal (model 6017, Kontron Electronics; Mountain View, Calif.). After the coordinates have been taken and stored, the Ulticam 2000 software so employed creates a "surface" file which is essentially a very detailed, high resolution representation of the actual facial impression that is derived by the Ulticam 2000 software. Information about the machining tools to be used can be supplied and a "cutter location" file can be generated. This file then can be used, in order of increasing machine tool depth, to drive the actual machining process. Actual machining can be done on a Hurco MB1 vertical CNC milling machine using a fourth axis rotary dividing head. Further machining and drilling is performed as necessary to obtain the desired passageways and outer shape.

Figure 6:
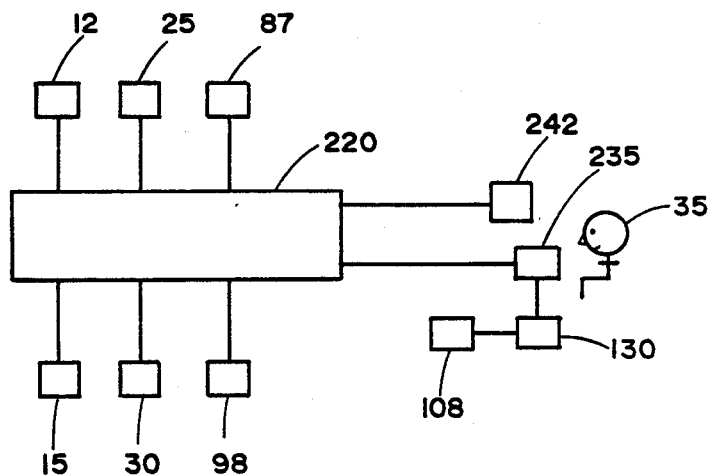
FIG. 6 is a schematic diagram of the configuration of the computer means with respect to the olfactometers and subject response means.

Referring to FIG. 6, each of olfactometers 12 and 15 are independently controlled and monitored by computer means 220. In particular, each of the electronic mass flow controllers of the olfactometers is independently controlled by the computer 220. For example, each electronic mass flow controller can be controlled by one channel of a suitable power supply/ readout unit, which is in turn controlled by voltage signals from an analog output interface card mounted in an Apple II E microcomputer. A suitable analog output card is available as Model AO03 from Interactive Structures, Malvern, Pa. The solenoid valves of the olfactometers are independently controlled by the computer 120. For example, each latching valve is controlled by a pair of solid state switching relays which are in turn controlled by two channels of a digital input/output interface card. A suitable digital input/output interface card is available as Model DI/09 from Interactive Structures. Operation of the valves using the computer will be apparent to the skilled artisan.

Photo-ionization detectors 87 and 98 are monitored independently by computer 220. For example, the current generated by each photo-ionization detector (which is proportional to the odorant concentration) is processed by a solid state electrometer and amplifier. The signals from each of the two photo-ionization detectors are sampled by one channel of an analog input interface card. A suitable analog input interface card is available as Model AI13 from Interactive Structures. The manner of monitoring the photo-ionization detectors using the computer will be apparent to the skilled artisan.

Valves 25 and 30 also are independently controlled and monitored by the computer 120. The computer interface card employed for controlling the solenoid valves conveniently also can be employed for controlling the flow valves. Operation will be apparent to the skilled artisan.

Fluctuations in pressure across the pneumotachograph 108 are sensed by pressure transducer 130 such as a commercially available Model MP45-14-871 from Validyne Corp., Northridge, Calif. Signals from pressure transducer 130 enter carrier demodulator 235 such as a commercially available Model CD 18-871 from Validyne Corp. The carrier demodulator converts the responses from pressure transducer to DC voltage signals which are in turn monitored by computer 220. In such a manner, voltage signal related to instantaneous voltage flow rate caused by subject's breathing can be used to compute changes in the subject's breathing rate, the volume of air breathed, and other such physiological changes. The computer interface card employed for monitoring the photo-ionization detectors also can be employed for monitoring the pneumotachograph.

The subject 35 can provide responses about the air samples and consequent stimulation through response means 242. It has been found that the practice of this invention is greatly facilitated by employing computer 220 for communicating instructions and prompts to the subject, and receiving responses from the subject. Thus, it is preferred that the computer include a response means 242 having a "mouse" or other suitable input capability for receiving responses from the subject. Such a capability not only eliminates the need for recording evaluations on a written ballot but also removes a potential directional influence on subject due to the visual availability of previously recorded responses. In addition to the "mouse," computer systems for receiving responses or input from a session coordinator are commercially available and include, for example, a touch sensitive computer monitor screen, a keyboard or similar means for positioning a cursor on the monitor screen and a bit pad with stylus. The computer means also allows a predetermined sequence or routing to be presented to the subject and may include pauses in the routine where appropriate. Suitable computer programs for leading a subject through the stimulation process are available to the skilled artisan and can take various forms. For example, a typical program can present initial instructions or prompts to the subject. At the appropriate point in the testing or evaluation session, a rating scale for a particular attribute, a questionnaire, or the like, can appear on the monitor screen. The subject then is requested to enter a rating for that attribute on the rating scale or other response. The data entered by the subject is stored by the computer for processing in accordance with separate data manipulation sequences programmed into the computer.

Figure 7:
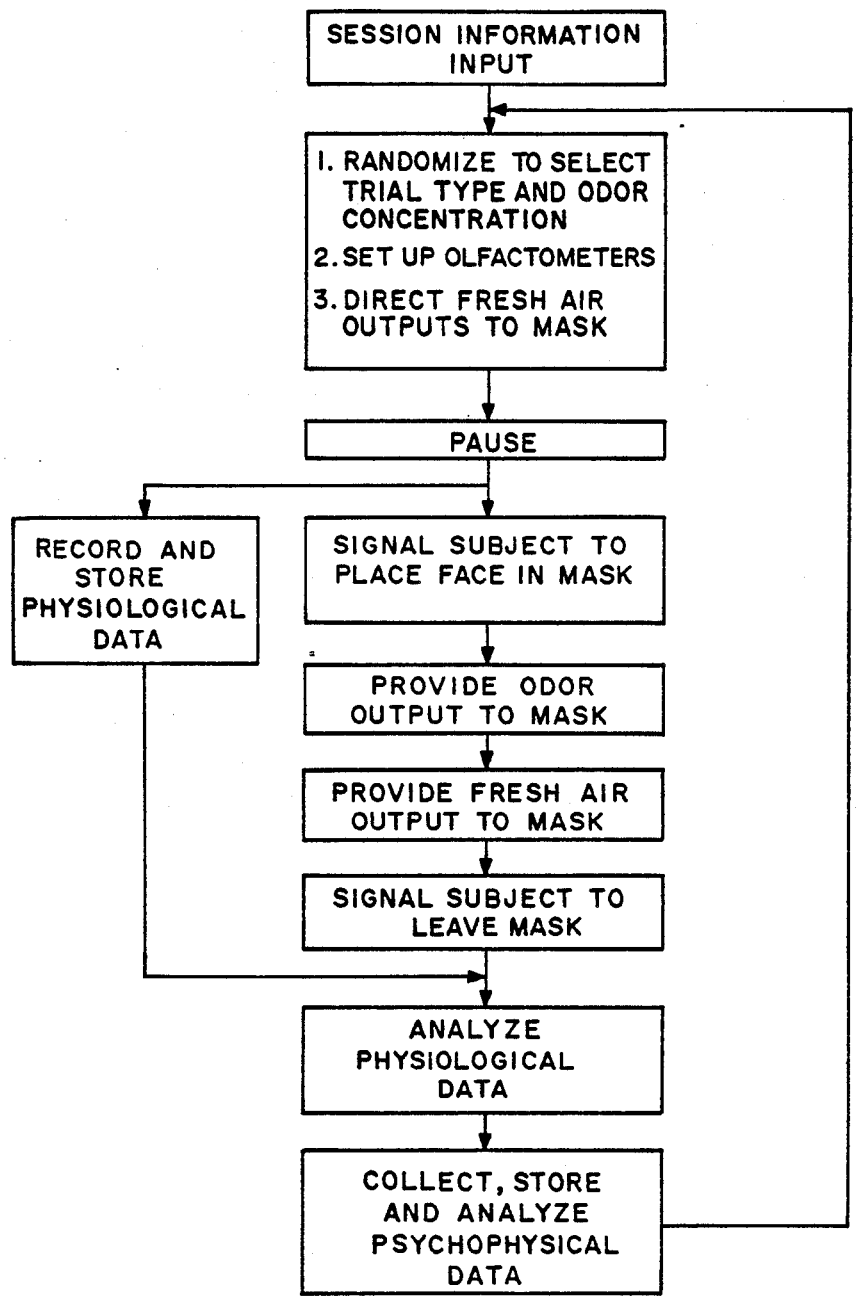
FIG. 7 is a flow chart of the control scheme of a test session.

Referring to FIG. 7, the session coordinator can enter session input information. Such information can include the name or identification number of the subject, the time or date of the sample session, the code number of the sample session, the trial type, the attributes to be evaluated, or any other desired information. The random number generated by the computer means then can be employed to randomly select the subsequent desired trial type and odorant concentration. The appropriate valves and electronic mass flow controllers of the olfactometers are set so that the selected concentrations of stimulant will be delivered by the nasal and ocular olfactometers. Until the actual presentation of the stimulant, the flow valves of both olfactometers are adjusted so that only clean air from both olfactometers is delivered to the mask. After a period of time (i.e., about 90 seconds), the subject is directed to place his/her face in the mask. The subject also is directed to breathe through his/her nose. Just prior (i.e., about 10 seconds) to such direction to the subject, operation of the apparatus for monitoring physiological responses (e.g., the video camera, the photo-ionization detectors, etc.) is commenced. Once the subject places his/her face in the mask, the flow valves of the olfactometers are positioned such that the desired concentration of stimulant is delivered to the eyes and/or nose of the subject. The subject is allowed to be subjected to contact with the stimulant for a desired period of time (e.g., about 10 seconds). The subject then is directed to remove his/her face from the mask. The appropriate valves and electronic mass flow controllers of the olfactometers then are set for the next trial. The subject is allowed to answer questions or provide comments concerning the trial (i.e., provide a psychophysical response). The psychophysical data as well as the information gathered by the photoionization detectors are stored by the computer means. The respiratory data is analyzed and stored by the computer means. Generally, a subsequent trial is commenced after a period of at least one minute after the previous trial is completed. Generally, the interval between successive stimulant presentations is about 90 seconds in order to allow the output levels of the two olfactometers to stabilize prior to each presentation.

In operation, the subject is tested repeatedly by subjecting the nose and/or eyes to odorant stimulation. Typically, each subject is presented with about 60 to about 80 sample trials within a test session. Within each test session, a selection can be made of one of four types of trials. The types of trials can be referred to as (i) clean air only (i.e., a reference or standard trial whereby only clean air is provided to both the eyes and nose of the subject); (ii) eyes only (i.e., stimulant is provided only to the eyes of the subject and clean air is provided to the nose of the subject); (iii) nose only (i.e., stimulant is provided only to the nose of the subject and clean air is provided to the eyes of the subject); and (iv) eyes and nose (i.e., stimulant is provided at independently controlled concentrations to both the eyes and nose of the subject).

Typically, the volume air flow rate from the nasal olfactometer to the nasal passage of the mask is about 10 l/min; and the volume airflow rate from the ocular olfactometer is about 1.5 l/min. The subject places his/her face within the mask. During the test period and for at least about 10 seconds afterward, the outputs of the photo-ionization detectors are sampled, the eye behavior of the subject is video recorded, and the breathing behavior of the subject is recorded. The flow valves are positioned such that the desired odorant-containing airflow is delivered to the mask. The flow valves then are positioned such that clean air passes from both olfactometers to the mask. The physiological data are stored, and the subject is instructed to remove his/her face from the mask and provide his/her psychophysical responses. For example, responses can be collected regarding sensory attributes such as odor strength, odor character, nasal irritation, eye irritation, overall acceptability, and the like.

For a clean air only trial, both outputs of the olfactometers are adjusted to deliver clean air. Generally, no change in a typical subject's breathing or eye blink rate is observed during such a trial. Furthermore, the typical subject generally reports little or no odor strength, nasal irritation or eye irritation.

For an eye only trial, the output of the nasal olfactometer is adjusted to deliver clean air, and the output of the ocular olfactometer is adjusted to deliver a selected odorant concentration. In particular, amyl acetate is positioned in a saturator tube of the ocular olfactometer, and the solenoid valves and flow valve thereof are positioned so as to provide a flow of air having an amyl acetate concentration of about 200 ppm. The concentration of the amyl acetate is monitored by the computer as the photo-ionization detector samples a volume flow rate of about 50 ml/min. A typical subject is observed to have an increased eye blink rate, as well as a very slight decrease in peak inspiratory volume flow rate. The typical subject reports (i) a moderate level of eye irritation, but (ii) no odor or nasal irritation.

For a nose only trial, the output of the ocular olfactometer is adjusted to deliver clean air, and the output of the nasal olfactometer is adjusted to deliver a selected odor concentration. In particular, amyl acetate is positioned in a saturator tube of the nasal olfactometer, and the solenoid valves and electronic mass flow controllers thereof are positioned so as to provide a flow of air having a concentration of amyl acetate of about 10 ppm. The concentration of the amyl acetate is monitored as described for the eye only trial. A typical subject maintains a constant eye blink rate and is observed to slightly increase the total volume of air breathed. The typical subject reports (i) no eye irritation, but (ii) some odor intensity and nasal irritation.

For an eye and nose trial, air containing amyl acetate is transferred to both the eyes and nose of the subject. A typical subject is observed to increase his/her eye blink rate, decrease his/her peak inspiratory volume flow rate and decrease his/her total volume of air breathed over time. The typical subject reports (i) a high level of eye irritation, and (ii) a low but noticeable odor strength and nasal irritation.

The use of the apparatus of this invention allows the skilled artisan to investigate the psychophysical and physiological effects of airborne chemicals with a high degree of precision. Both separate and combined effects of airborne stimulant to the eyes and nose of the same subject can be investigated simultaneously. Thus, information concerning the physiology of odor perception as a result of stimulation of the trigeminal and/or olfactory neural systems can be obtained in a very efficient and effective manner. Of particular interest is an automated apparatus having a self-monitoring means such that large amounts of high quality human response data can be collected. The human response data concerning airborne chemicals is useful in providing information concerning environmental air quality, fragrances, and the like.

The apparatus of this invention also is useful in the field of electroencephalography (EEG) as applied to the sense of smell. For example, precise information concerning the subject's breathing as well as concerning the actual stimulant presented to the subject can be combined with EEG information recorded from the subject's scalp. The apparatus also is useful for testing and hence diagnosing subjects who have sustained damage to the olfactory or trigeminal pathways. For example, the ability to stimulate independently the eye and/or nose of the subject allows the skilled artisan to accurately characterize their roles in mediating the perceptual and physiological responses to odorants.

It is understood that the particular embodiments and examples described herein are only illustrative of the principles of this invention, and that various modifications can be made by those skilled in the art without departing from the scope and spirit of the invention.

What is claimed is:

1. An apparatus for (i) stimulating the nose of a human subject in a controlled manner, and (ii) collecting data regarding the stimulation provided to the subject, the apparatus comprising:
   (a) source of stimulant;
   (b) means for transferring controlled amounts of the stimulant within a gaseous medium to the nose of the subject;
   (c) computer means for recording at least one psychophysical response of the subject to the stimulant; and
   (d) means for recording at least one physiological response of the subject to the stimulant.

2. The apparatus of claim 1 further comprising means for altering the identity and amount of stimulant within the gaseous medium which is transferred to the nose of the subject.

3. The apparatus of claim 1 or 2 wherein the controlled amount of stimulant within the gaseous medium can range from the absence of the stimulant to gaseous medium saturated with the stimulant.

4. The apparatus of claim 1 further comprising computer means for controlling the amount of stimulant within the gaseous medium.

5. The apparatus of claim 1 or 2 further comprising means for monitoring the instantaneous stimulant concentration within the gaseous medium.

6. An apparatus for (i) stimulating the eyes of a human subject in a controlled manner, and (ii) collecting data regarding the stimulation provided to the subject, the apparatus comprising:
   (a) source of stimulant;
   (b) means for transferring controlled amounts of the stimulant within a gaseous medium to the eyes of the subject;
   (c) means for recording at least one psychophysical response of the subject to the stimulant; and
   (d) means for recording at least one physiological response of the subject to the stimulant.

7. The apparatus of claim 6 further comprising means for altering the identity and amount of stimulant within the gaseous medium which is transferred to the eyes of the subject.

8. The apparatus of claim 6 or 7 wherein the psychophysical responses of the subject are recorded by computer means.

9. The apparatus of claim 6 or 7 wherein the controlled amount of stimulant within the gaseous medium can range from the absence of the stimulant to gaseous medium saturated with the stimulant.

10. The apparatus of claim 6 further comprising computer means for controlling the amount of stimulant within the gaseous medium and for recording psychophysical responses of the subject.

11. The apparatus of claim 6 or 7 further comprising means for monitoring the instantaneous stimulant concentration within the gaseous medium.

12. An apparatus for (i) simultaneously stimulating the eyes and nose of a human subject independently and in a controlled manner, and (ii) collecting data regarding the stimulation provided to the subject, the apparatus comprising:
   (a) source of stimulant;
   (b) means for transferring controlled amounts of the stimulant within a gaseous medium to the eyes and/or nose of the subject; and
   (c) means for recording physiological responses of the subject to the stimulant.

13. The apparatus of claim 12 including means for recording the breathing pattern of the subject.

14. The apparatus of claim 12 including means for recording physiological eye responses of the subject.

15. The apparatus of claim 12 wherein the stimulant is transferred to the eyes and nose of the subject within a flow of air of controlled flow rate.

16. The apparatus of claim 12 further comprising means for altering the identity and amount of stimulant within the gaseous medium which is transferred to the eyes and/or nose of the subject.

17. The apparatus of claim 12 comprising separate sources of stimulant for the simultaneous and independent stimulation of the eyes and nose of the subject.

18. The apparatus of claim 12, 16 or 17 comprising a mask fitted for the face of the subject such that gaseous medium can be independently transferred to the eyes and nose of the subject.

19. The apparatus of claim 12, 16 or 17 wherein the controlled amount of stimulant within the gaseous medium can range from the absence of the stimulant to gaseous medium saturated with the stimulant.

20. An apparatus for (i) simultaneously stimulating the eyes and nose of a human subject independently in a controlled manner, and (ii) collecting data regarding the stimulation provided to the subject, the apparatus comprising:
   (a) source of stimulant;
   (b) means for transferring controlled amounts of the stimulant within a gaseous medium to the eyes and/or nose of the subject; and
   (c) means for recording psychophysical responses of the subject to the stimulant.

21. The apparatus of claim 20 wherein the stimulant is transferred to the eyes and nose of the subject within a flow of air of controlled flow rate.

22. The apparatus of claim 20 further comprising means for altering the identity and amount of stimulant within the gaseous medium which is transferred to the eyes and/or nose of the subject.

23. The apparatus of claim 20 wherein the psychophysical responses of the subject are recorded by computer means.

24. The apparatus of claim 20 comprising separate sources of stimulant for the simultaneous and independent stimulation of the eyes and nose of the subject.

25. The apparatus of claim 20, 22 or 24 comprising a mask fitted for the face of the subject such that gaseous medium can be independently transferred to the eyes and nose of the subject.

26. The apparatus of claim 20, 22 or 24 wherein the controlled amount of stimulant within the gaseous medium can range from the absence of the stimulant to gaseous medium saturated with the stimulant.

27. The apparatus of claim 20 further comprising computer means for controlling the amount of stimulant within the gaseous medium and for recording psychophysical responses of the subject.

28. An apparatus for (i) simultaneously stimulating the eyes and nose of a human subject independently and in a controlled manner, and (ii) collecting data regarding the stimulation provided to the subject, the apparatus comprising:
(a) source of stimulant;
(b) means for transferring controlled amounts of the stimulant within a gaseous medium to the eyes and/or nose of the subject;
(c) means for recording psychophysical responses of the subject to the stimulant; and
(d) means for recording physiological responses of the subject to the stimulant.

29. The apparatus of claim 28 further comprising means for altering the identity and amount of stimulant within the gaseous medium which is transferred to the eyes and/or nose of the subject.

30. The apparatus of claim 28 or 29 including means for recording the breathing pattern of the subject.

31. The apparatus of claim 28 or 29 including means for recording physiological eye responses of the subject.

32. The apparatus of claim 28 or 29 wherein the stimulant is transferred to the eyes and nose of the subject within a flow of air of controlled flow rate.

33. The apparatus of claim 28 or 29 wherein the psychophysical responses of the subject are recorded by computer means.

34. The apparatus of claim 28 comprising separate sources of stimulant for the simultaneous and independent stimulation of the eyes and nose of the subject.

35. The apparatus of claim 28 or 29 comprising a mask fitted for the face of the subject such that gaseous medium can be independently transferred to the eyes and nose of the subject.

36. The apparatus of claim 28 or 29 wherein the controlled amount of stimulant within the gaseous medium can range from the absence of the stimulant to gaseous medium saturated with the stimulant.

37. The apparatus of claim 28 or 29 further comprising computer means for controlling the amount of stimulant within the gaseous medium and for recording psychophysical responses of the subject.

* * * * *